United States Patent [19]

Flynn et al.

[11] Patent Number: 5,280,028

[45] Date of Patent: Jan. 18, 1994

[54] BENZIMIDAZOLE COMPOUNDS

[75] Inventors: Daniel L. Flynn, Mundelein; Alan E. Moormann, Skokie, both of Ill.

[73] Assignee: G. D. Searle & Co., Chicago, Ill.

[21] Appl. No.: 903,835

[22] Filed: Jun. 24, 1992

[51] Int. Cl.$^5$ ............... C07D 451/00; C07D 471/00; A61K 31/41; A61K 31/435

[52] U.S. Cl. .......................... 514/294; 546/93; 546/94

[58] Field of Search ............... 546/93, 94; 514/294

[56] References Cited

U.S. PATENT DOCUMENTS

| | | | |
|---|---|---|---|
| 4,083,985 | 4/1978 | Cohen et al. | 546/94 |
| 5,137,893 | 8/1992 | Becker et al. | 514/293 |
| 5,140,023 | 8/1992 | Becker et al. | 514/214 |

FOREIGN PATENT DOCUMENTS 0309423 9/1988 European Pat. Off. .... C07D 451/12

OTHER PUBLICATIONS

Schiantarelli et al. Pharmacological Research 22, Supp. 2 453 Jan. 1990.

A. Dumuis et al. Azabicycloalkylbenzimidazolone derivatives as etc. Naunyn-Schmiedeberg;s Arch Pharmacol 343 245-251 Jan. 1991.

M. Turconi et al. Synthesis of a New Class of etc. J. Med. Chem. 33, No. 8 2101-2108 Jan. 1990.

*Primary Examiner*—C. Warren Ivy
*Assistant Examiner*—Phyllis G. Spivack
*Attorney, Agent, or Firm*—Cynthia S. Kovacevic; Roger A. Williams

[57] ABSTRACT

This invention relates to compounds useful in treating HT$_4$ and/or HT$_3$ mediated conditions of the formula

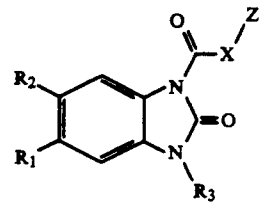

or a pharmaceutically acceptable salt thereof wherein R$_1$ and R$_2$ are independently selected from the group consisting of hydrogen, alkoxy, halogen, amino, monoalkylamino, dialkylamino, acylamino and alkylsulfonylamino; R$_3$ is selected from the group consisting of H, alkyl and cycloalkyl; X is NH or O; Z is selected from the group consisting of

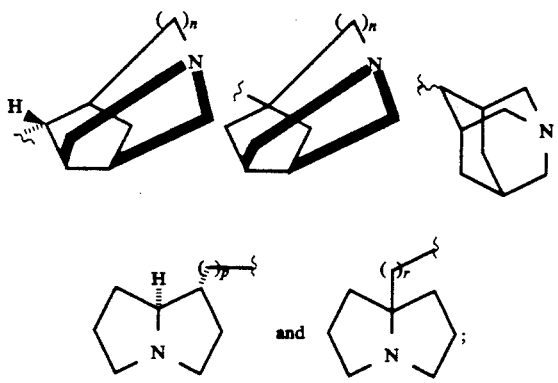

n and r are independently 1 or 2; p is 0 or 1; pharmaceutical compositions containing the compounds and a method for treating serotonin mediated condition with the compositions which act as 5-HT$_4$ agonists or antagonists and/or 5-HT$_3$ antagonists.

38 Claims, No Drawings

BENZIMIDAZOLE COMPOUNDS

BACKGROUND OF THE INVENTION

The present invention relates to pharmaceutical agents (compounds) which act as 5-HT$_4$ agonists or antagonists and/or 5-HT$_3$ antagonists in mammals. As 5-HT$_4$ agonists these agents are useful in the treatment of hypomotility disorders of the gastrointestinal (GI) tract including reflux esophagitis, non-ulcer dyspepsia, gastroparesis, ileus, irritable bowel syndrome (constipation predominant) and constipation. Additionally, 5-HT$_4$ agonists are useful for the treatment of learning and memory disorders and as cardiovascular inotropic agents. As 5-HT$_4$ antagonists these compounds are useful in the treatment of motility disorders of the GI tract such as diarrhea and irritable bowel syndrome (diarrhea predominant). As 5-HT$_3$ antagonists these compounds are useful for treating emesis (caused by cancer chemotherapy or post-operative), anxiety, cognitive disorders, drug abuse (either cravings or withdrawal syndrome) and irritable bowel syndrome (diarrhea predominant).

Serotonin (5-hydroxytryptanine; 5-HT) functions as a neurotransmitter in the mammalian central nervous system (CNS) and in the periphery. Serotonergic neurons regulate a wide variety of sensory, motor and cortical functions. Additionally serotonin regulates enteric reflexes, mediates contraction of the vascular smooth muscle and platelet shape change and aggregation and as such effects such diverse systems as the cardiovascular system and gastrointestinal system, in addition to the central nervous system.

Pharmacological and physiological studies show that the activity of serotonin is mediated by several distinct cell surface receptor subtypes. These receptor subtypes either transduce extracellular signals by activating GTP-binding proteins (G-protein-coupled receptor subtypes) or activate the opening of nonselective cation channels to promote fast, depolarizing responses in neurons (ligand-gated ion channel receptor subtypes). 5-HT$_4$ belongs to the former category while 5-HT$_3$ belongs to the latter. Agents which interact with these receptors thereby modulate a variety of ion channels and intracellular messenger signaling pathways thereby extending the flexibility of serotonings activity and eliciting a multitude of cellular and physiological responses. P. Bonate, *Clinical Neuropharmacology*, Vol. 14, No. 1, pp. 1–16 (1991).

European Patent application 309,423 discloses azabicyclo substituted benzimidazoline-2-oxo-1-carboxylic acid derivatives which are useful as 5-HT receptor antagonists.

Dumuis et al., *Nauyn-Schmiedeberg's Arch Pharmacol*, (1991) 343:245-251 disclose azabicycloalkyl benzimidazolone derivatives as potent agonists at the 5-HT$_4$ receptor.

In *Pharmacological Research*, Vol. 22, Supplement 2, (1990) Schiantarelli et al. disclose two benzimidazolone compounds useful as 5-HT$_3$ antagonists and 5-HT$_4$ agonists.

There is a need in the area of serotonin regulation for agents with broad clinical usefulness. Serotonin is one of the newer neurotransmitters to be recognized for physiological importance and agents which interact with 5-HT receptors are currently the focus of much research. P. Bonate, *Clinical Neuropharmacology*, Vol. 14, No. 1, pp. 1–16 (1991). Accordingly, it is the object of this invention to produce compounds for use as pharmaceutical agents which will exhibit 5-HT$_4$ agonist or antagonist activity and/or 5-HT$_3$ antagonist activity in mammals. The compounds of the present invention meet the need for an agent which has broad clinical usefulness for treating serotonin mediated conditions in mammals by administering a therapeutically effective amount of the compounds to act as 5-HT$_4$ agonists or antagonists and/or 5-HT$_3$ antagonists.

SUMMARY OF THE INVENTION

This invention relates to compounds of the Formula I

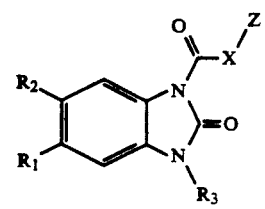

or a pharmaceutically acceptable salt thereof wherein $R_1$ and $R_2$ are independently selected from the group consisting of hydrogen, alkoxy, halogen, amino, monoalkylamino, dialkylamino, acylamino and alkylsulfonylamino;

$R_3$ is selected from the group consisting of H, alkyl and cycloalkyl;

X is NH or O;

Z is selected from the group consisting of

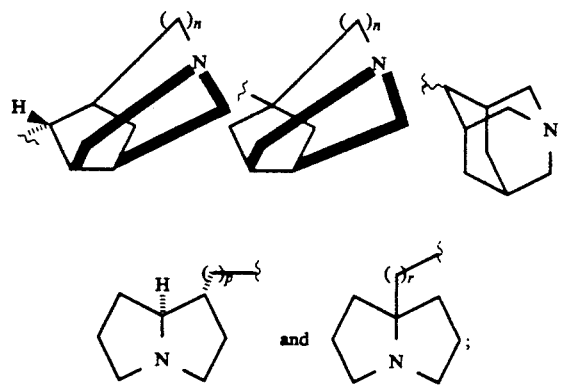

n and r are independently 1 or 2; and
p is 0 or 1.

The present invention also provides pharmaceutical compositions comprised of a therapeutically effective amount of the compounds of Formula I in combination with a pharmaceutically acceptable carrier and a method for treating serotonin mediated conditions with said compositions which act as 5-HT$_4$ agonists or antagonists and/or 5-HT$_3$ antagonists.

DETAILED DESCRIPTION OF THE INVENTION

This invention encompasses compounds of the Formula I as previously described.

Within the class of compounds defined by Formula I, there is a sub-class of preferred compounds represented by Formula II:

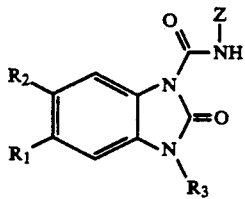

or a pharmaceutically acceptable salt thereof wherein $R_1$ and $R_2$ are independently selected from the group consisting of hydrogen, alkoxy, halogen, amino, monoalkylamino, dialkylamino, acylamino and alkylsulfonylamino;

$R_3$ is selected from the group consisting of H, alkyl and cycloalkyl;

Z is selected from the group consisting of

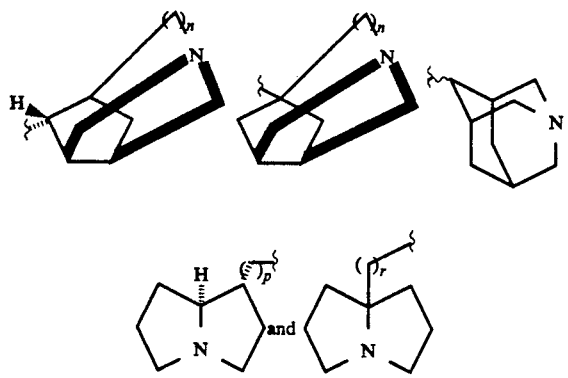

n and r are independently 1 or 2; and
p is 0 or 1.

A more preferred subclass of compounds included within Formula II are:

endo-N-(1-azatricyclo[3.3.1.1$^{3,7}$]decan-4-yl)-3-ethyl-2,3-dihydro-2-oxo-1H-benzimidazole-1-carboxamide;

exo-N-(1-azatricyclo[3.3.1.1$^{3,7}$]decan-4-yl)-3-ethyl-2,3-dihydro-2-oxo-1H-benzimidazole-1-carboxamide;

endo-N-(1-azatricyclo[3.3.1.1$^{3,7}$]decan-4-yl)-6-chloro-2,3-dihydro-3-(1-methylethyl)-2-oxo-1H-benzimidazole-1-carboxamide;

endo-N-(1-azatricyclo[3.3.1.1$^{3,7}$]decan-4-yl)-5-chloro-2,3-dihydro-3-(1-methylethyl)-2-oxo-1H-benzimidazole-1-carboxamide;

endo-N-(1-azatricyclo[3.3.1.1$^{3,7}$]decan-4-yl)-6-chloro-3-ethyl-2,3-dihydro-2-oxo-1H-benzimidazole-1-carboxamide;

exo-N-(1-azatricyclo[3.3.1.1$^{3,7}$]decan-4-yl)-6-chloro-3-ethyl-2,3-dihydro-2-oxo-1H-benzimidazole-1-carboxamide;

endo-N-(1-azatricyclo[3.3.1.1$^{3,7}$]decan-4-yl)-5-chloro-3-ethyl-2,3-dihydro-2-oxo-1H-benzimidazole-1-carboxamide;

exo-N-(1-azatricyclo[3.3.1.1$^{3,7}$]decan-4-yl)-5-chloro-3-ethyl-2,3-dihydro-2-oxo-1H-benzimidazole-1-carboxamide;

cis-N-[(hexahydro-1H-pyrrolizin-1-yl)methyl]-2,3-dihydro-3-(1-methylethyl)-2-oxo-1H-benzimidazole-1-carboxamide;

5-chloro-N-[2-(hexahydro-7aH-pyrrolizin-7a-yl)ethyl]-2,3-dihydro-3-(1-methylethyl)-2-oxo-1H-benzimidazole-1-carboxamide;

N-[2-(hexahydro-7aH-pyrrolizin-7a-yl)ethyl]-2,3-dihydro-3-(1-methylethyl)-2-oxo-1H-benzimidazole-1-carboxamide; and N-[(hexahydro-7aH-pyrrolizin-7a-yl)methyl]-2,3-dihydro-3-(1-methylethyl)-2-oxo-1H-benzimidazole-1-carboxamide exo-N-(1-azatricyclo[3.3.1.1$^{3,7}$]decan-4-yl)-2,3-dihydro-3-(1-methylethyl)-2-oxo-1H-benzimidazole-1-carboxamide endo-N-(1-azatricyclo[3.3.1.1$^{3,7}$]decan-4-yl)-2,3-dihydro-3-(1-methylethyl)-2-oxo-1H-benzimidazole-1-carboxamide exo-N-(1-azatricyclo[3.3.1.1$^{3,7}$]decan-4-yl)-6-chloro-2,3-dihydro-3-(1-methylethyl)-2-oxo-1H-benzimidazole-1-carboxamide exo-N-(1-azatricyclo[3.3.1.1$^{3,7}$]decan-4-yl)-2,3-dihydro-3-(1-methylethyl)-2-oxo-1H-benzimidazole-1-carboxamide 6-fluoro-N-[2-(hexahydro-7aH-pyrrolizin-7a-yl)ethyl]-2,3-dihydro-3-(1-methylethyl)-2-oxo-1H-benzimidazole-1-carboxamide N-[2-(hexahydro-7aH-pyrrolizin-7a-yl)ethyl]-2,3-dihydro-6-methoxy-3-(1-methylethyl)-2-oxo-1H-benzimidazole-1-carboxamide 3-ethyl-N-[2-(hexahydro-7aH-pyrrolizin-7a-yl)ethyl]-2,3-dihydro-2-oxo-1H-benzimidazole-1-carboxamide.

N-(hexahydro-1H-2,5$\beta$-methano-3a$\alpha$,6a$\alpha$-cyclopenta[c]pyrrol-4$\alpha$-yl)-2,3-dihydro-3-(1-methylethyl)-2-oxo-1H-benzimidazole-1-carboxamide Included within the classes and subclasses of compounds embraced by Formulas I–II are isomeric forms of the described compounds including diastereoisomers and enantiomers and tautomeric forms of the described compounds. Pharmaceutically acceptable salts of such compounds are also included as well as pharmaceutically acceptable salts of such isomers and tautomers.

In the structures herein a bond drawn across a bond in a ring indicates that the bond can be to any available atom of the ring structure.

The term "pharmaceutically acceptable salt," as used herein, refers to conventionally accepted pharmaceutical salts prepared by processes which are well known to those of ordinary skill in the art. [See for example, S. M. Berge, et al., "Pharmaceutical Salts," J. Pharm. Sci., 66:1–19 (1977)).

The term "composition" as used herein means a product which results from the mixing or combining of more than one element or ingredient.

The term "pharmaceutically acceptable carrier" as used herein means a pharmaceutically-acceptable material, composition or vehicle, such as a liquid or solid filler, diluent, excipient, solvent or encapsulating material, involved in carrying or transporting a chemical agent from one organ or portion of the body to another organ or portion of the body.

The term "therapeutically effective amount" shall mean that amount of drug or pharmaceutical agent that will elicit the biological or medical response of a tissue, system or animal that is being sought by a researcher or clinician.

The term "alkyl" as used herein means a univalent hydrocarbon radical having from one to twelve carbon atoms, more preferably from one to six carbon atoms and derived by the removal of a single hydrogen atom from a straight or branched chain saturated hydrocarbon. Representative of such radicals are methyl, ethyl, n-propyl, isopropyl, n-butyl, sec-butyl, isobutyl, tertbutyl, 2-ethylhexyl, n-octyl, 2,4-dimethylpentyl and the like.

The term "alkoxy" as used herein means an alkyl radical, as defined above having one or more oxygen atoms attached thereto. Representative alkoxy groups include methoxy, ethoxy, propoxy, tert-butoxy and the like.

The term halogen as used herein means a fluoro, chloro, bromo or iodo radical.

The term "monoalkylazino" as used herein is represented by the radical —NHR$_4$ wherein R$_4$ is an alkyl group as previously described.

The term "dialkylazino" as used herein is represented by the radical —NR$_4$R$_5$ wherein R$_4$ and R$_5$ are the same or different alkyl groups, as defined above.

The term "acylamino" as used herein is represented by the radical

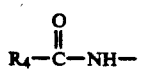

wherein R$_4$ is an alkyl group as described above.

The term "alkylsulfonylanino" as used herein is represented by the radical R$_4$—SO$_2$—NH— wherein R$_4$ is an alkyl group as defined above.

The term "cycloalky" as used herein means an alicyclic radical with from 3 to 6 carbon atoms. Examples of suitable cycloalkyl radicals includes cyclopropyl, cyclopropenyl, cyclobutyl, cyclopentyl, cyclohexyl, 2-cyclohexen-1-yl and the like.

The compounds herein exhibit 5-HT$_4$ agonism or antagonism and/or 5-HT$_3$ antagonism. The 5-HT$_3$ antagonist activity possessed by the compounds of this invention was determined by the radioligand receptor binding assay as described herein and in the in vivo Bezold-Jarisch reflex procedure. 5-HT$_4$ agonist activity was determined in the in vitro rat tunica muscularis mucosas (TMM) assay. (Baxter et al., Naunyn Schmied Arch. Pharmacol, 1991, 343, 439). The 5-HT$_4$ agonist or antagonist activity and/or 5-HT$_3$ antagonist activity of the compounds of the invention herein, can be determined by the assays as described herein, without undue experimention.

By virtue of their activity as 5-HT$_4$ agonists or antagonists and/or 5-HT$_3$ antagonists the compounds of Formula I and II are useful in treating serotonin mediated conditions such as gastrointestinal motility disorders, emesis, anxiety, cognitive disorders and other CNS disorders. As used herein 5-HT$_4$ agonist mediated conditions of the gastrointestinal tract include reflux esophagitis, non-ulcer dyspepsia, gastroparesis, ileus, irritable bowel syndrome (constipation predominant), constipation, and the like. As used herein 5-HT$_4$ antagonist mediated conditions of the GI tract include diarrhea, irritable bowel syndrome (diarrhea predominant) and the like. As used herein 5-HT$_3$ antagonist mediated conditions include emesis due to either cancer chemotherapy or post-operative, anxiety, cognitive disorders, drug abuse (either cravings or withdrawal syndrome), irritable bowel syndrome (diarrhea predominant) and the like. A physician or veterinarian of ordinary skill can readily determine whether a subject exhibits such a serotonin mediated condition.

The compounds of the present invention can be administered in such oral dosage forms as tablets, capsules, softgels, pills, powders, granules, elixirs or syrups. The compounds can also be administered intravascularly, intraperitoneally, subcutaneously, intramuscularly or topically using forms known to the pharmaceutical art. In general the preferred form of administration is oral.

For the orally administered pharmaceutical compositions and methods of the present invention, the foregoing active ingredients will typically be administered in admixture with suitable pharmaceutical diluents, excipients or carriers (collectively referred to hereinafter as "carrier" materials). Such carrier materials are suitably selected with respect to the intended form of administration and consistent with conventional pharmaceutical practices.

For example, for oral administration in the form of tablets or capsules, a therapeutically effective amount of one or more compounds of the present invention can be combined with any oral pharmaceutically acceptable inert carrier such as lactose, starch, sucrose, cellulose, magnesium stearate, calcium sulfate and the like or various combinations thereof. For oral administration in liquid forms, such as in softgels, elixirs, syrups and the like, a therapeutically effective amount of the active drug components can be combined with any oral pharmaceutically acceptable inert carrier such as water, ethanol, polyethylene glycol, vegetable oils, propylene glycol, benzylalcohol and the like or various combinations thereof.

When desired or necessary, suitable binders, lubricants, disintegrating agents, preservatives, and coloring or flavoring agents can also be incorporated into the mixture. Suitable binders include starch, gelatin, natural sugars, corn sweeteners, natural and synthetic gums and waxes and the like, or combinations thereof. Lubricants can include boric acid, sodium benzoate, sodium acetate, sodium chloride and the like, or combinations thereof. Disintegrators include without limitation starch, methylcellulose, agar, bentonite, guar gum and the like, or combinations thereof.

For intravascular, intraperitoneal, subcutaneous or intramuscular administration, one or more compounds of the present invention can be combined with a suitable carrier such as water, saline, aqueous dextrose and the like. For topical administration therapeutically effective amounts of one or more compounds of the present invention can be combined with pharmaceutically acceptable creams, oils, waxes, gels and the like.

Regardless of the route of administration selected, a therapeutically effective amount of the compounds of the present invention are formulated into pharmaceutically acceptable dosage forms by conventional methods known to those skilled in the art. The dosages for preventing or treating serotonin mediated conditions with the compounds of the present invention is determined in accordance with a variety of factors, including the type, age, weight, sex and medical condition of patient, the severity of the condition, the route of administration and the particular compound employed in the treatment. A physician or veterinarian of ordinary skill can readily determine and prescribe an effective amount of drug required to prevent or arrest progress of the condition. In so proceeding, the physician or veterinarian could employ relatively low doses at first and subsequently increase the dose until a maximum response is obtained. The daily doses of the compounds of the invention are ordinarily in the range of about 1 to 1000 mg, more preferably in the range of about 10 to 500 mg.

The compounds of this invention are generally prepared according to reaction schemes I and II.

Scheme I

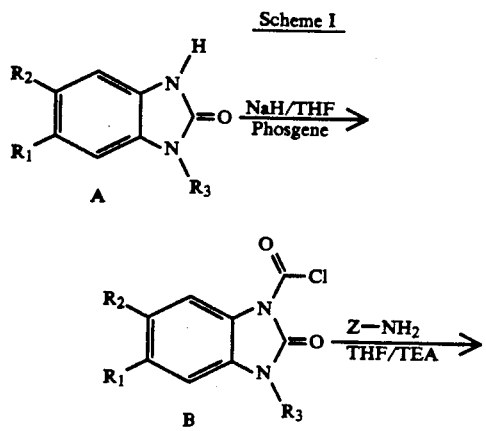

Wherein R1 is H or Cl; R2 is H, F, Cl, OMe.
Z is as defined above.
THF = tetrahydrofuran
TEA = triethylamine

Scheme II

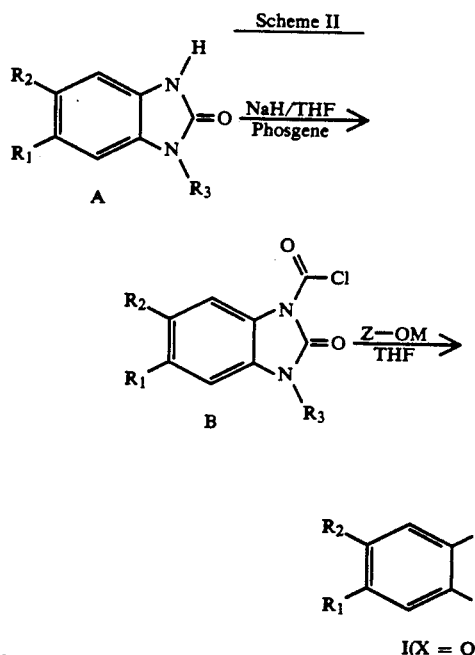

Wherein R1 is H or Cl; R2 is H, F, Cl, OMe.
Z is as defined above.
M = Na, K, Cs or H
THF = tetrahydrofuran
TEA = triethylamine As shown in reaction Scheme I the 3-unsubstituted benzimidazolones A are reacted with a base (preferably sodium hydride) in an inert etheral solvent (preferably tetrahydrofuran) to generate the sodium salt, which is reacted with phosgene to produce the 3-carbamoyl-chloride substituted benzimidazolone B. This intermediate is reacted with the appropriate amine (Z-NH2, as defined above) in an inert solvent (preferably tetrahydrofuran) in the presence of a base (preferably triethylamine) to afford the desired compounds of formulae II.

Alternatively, as shown in reaction Scheme II, intermediate B is reacted with the appropriate alcohol (Z-OH, as defined above) or its metal salt (preferably Na, K, or Cs; formed by reaction with, by illustration, sodium hydride, potassium hydride, cesium carbonate) in an inert solvent (preferably tetrahydrofuran or dimethylformamide) at either ambient or elevated temperature (50° C. to 110° C.) to afford desired compounds of formulae I, wherein X=O.

The following examples illustrate the methods used to prepare the compounds of this invention. These examples are given by way of illustration only and are not meant to be construed as limiting the invention in spirit or scope, as many modifications in materials and methods will be apparent from this disclosure to one having ordinary skill in the art.

EXAMPLE 1

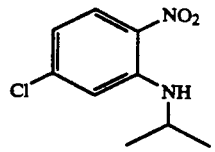

5-chloro-N-isopropyl-2-nitroaniline 5-chloro-2-nitroaniline (8.6 g; 0.05 mole), 2,2-dimethoxypropane (10.0 ml; 0.09 mole) and trifluoroacetic acid [TFA] (4.0 ml; 0.005 moles) were dissolved in toluene (100 ml) and stirred for 1 hr. A boron/pyridine complex (hereinafter BH3 * pyridine) (5.0 ml; 0.05 moles) was added in 1.0 ml increments. The reaction was exothermic, and the reaction progress was monitored by tlc (40%EtOAc/hexane). Additional TFA, BH3 * pyridine and 2,2-dimethoxypropane were added until the tlc indicated that the 5-chloro-2-nitroaniline was consumed. The reaction mixture was placed on a bed of silica and eluted with toluene. The product was the first major component to elute, which produced 6.6 g (61%) of a yellow crystalline solid.

$C_9H_{10}ClN_2O_2$ M.W. 213.63.

| Elements | Calc | Found |
|---|---|---|
| Carbon | 50.36 | 50.27 |
| Hydrogen | 5.17 | 5.17 |
| Nitrogen | 13.05 | 12.97 |
| Chlorine | 16.52 | 15.92 |

EXAMPLE 2

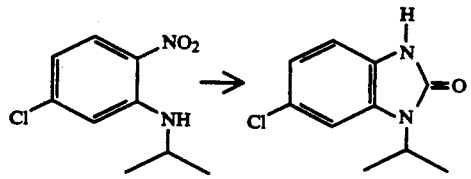

5-chloro-N-isopropyl-2-nitroaniline → 6-chloro-1,3-dihydro-1-(1-methylethyl)-2H-benzimidazol-2-one 5-chloro-N-isopropyl-2-nitroaniline (6.5 g; 0.03 mole) was dissolved in MeOH (330 ml) and hydrogenated at room temperature, at 5.0 psi over Ra-Ni for 1.5 hr. at which time the theoretical hydrogen uptake had been achieved. The reaction mixture was filtered and the filtrate was concentrated. The residue was dissolved in $CH_2Cl_2$ (250 ml) and triphosgene (3.06 g; 0.01 mole) dissolved in 25 ml of $CH_2Cl_2$ was added. The reaction was exothermic. The reaction mixture was stirred for 1 hr. and then concentrated. The residue was placed on a bed of silica and eluted with $EtOH/CH_2Cl_2$ using a gradient from 5%→>40% EtOH. The fractions containing the product were combined and concentrated to yield 2.7 g (43%) of a purple-white solid.

$C_{10}H_{11}ClN_2O$ M.W. 210.65.

| Elements | Calc | Found |
|---|---|---|
| Carbon | 57.01 | 56.61 |
| Hydrogen | 5.26 | 5.29 |
| Nitrogen | 13.30 | 13.19 |
| Chlorine | 16.83 | 17.20 |

EXAMPLE 3

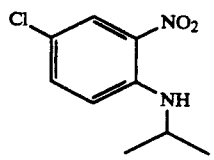

4-chloro-N-isopropyl-2-nitroaniline 4-chloro-2-nitroaniline (8.6 g; 0.05 mole), 2,2-dimethoxypropane (10.0 ml; 0.9 mole) and trifluoroacetic acid [TFA] (4.0 ml; 0.005 moles) were dissolved in toluene (100 ml) and stirred for 1 hr. $BH_3$ * pyridine (5.0 ml; 0.05 moles) was added in 1.0 ml increments. The reaction was exothermic, and the reaction progress was monitored by tlc 40%EtOAc/Hexane. Additional TFA, $BH_3$ * pyridine and 2,2-dimethoxypropane were added until the tlc indicated that the 4-chloro-2-nitroaniline was consumed. The reaction mixture was placed on a bed of silica and eluted with toluene. The product was the first major component to elute, which produced 8.4 g (78%) of a yellow crystalline solid.

$C_9H_{10}ClN_2O_2$ M.W. 213.63.

| Elements | Calc | Found |
|---|---|---|
| Carbon | 50.36 | 50.44 |
| Hydrogen | 5.17 | 5.26 |
| Nitrogen | 13.05 | 12.96 |
| Chlorine | 16.52 | 16.22 |

EXAMPLE 4

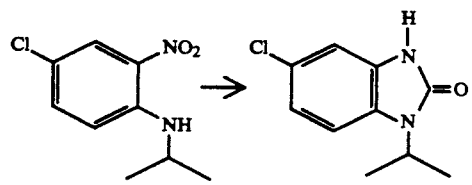

4-chloro-N-isopropyl-2-nitroaniline →5-chloro-1,3-dihydro-1-(1-methylethyl)-2H-benzimidazol-2-one 4-chloro-N-isopropyl-2-nitroaniline (8.3 g; 0.0389 mole) was dissolved in MeOH (330 ml) and hydrogenated at room temperature, at 5.0 psi over Ra-Ni for 1.5 hr. at which time the theoretical hydrogen uptake had been achieved. The reaction mixture was filtered and the filtrate was concentrated. The residue was dissolved in $CH_2Cl_2$ (250 ml) and triphosgene (3.9 g; 0.014 mole) dissolved in 25 ml of $CH_2Cl_2$ was added. The reaction was exothermic. The reaction mixture was stirred for 1 hr. and then concentrated. The solid was triturated with water and filtered, washed with $Et_2O$ and suction dried which produced 5.7 g (69.5%) of a purple-white solid.

$C_{10}H_{11}ClN_2O$ M.W. 210.65.

| Elements | Calc | Found |
|---|---|---|
| Carbon | 57.01 | 56.89 |
| Hydrogen | 5.26 | 5.28 |
| Nitrogen | 13.30 | 13.29 |
| Chlorine | 16.83 | 16.54 |

EXAMPLE 5

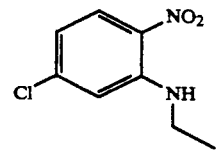

5-chloro-N-ethyl-2-nitroaniline 5-chloro-2-nitroaniline (17.2 g; 0.1 mole), acetaldehyde diethyl acetal (Acetal) (21.1 ml; 0.15 mole) and TFA (7.7 ml; 0.1 moles) were dissolved in toluene (500 ml) and stirred for 1 hr. $BH_3$ * pyridine (10.0 ml; 0.1 moles) was added in 1.0 ml increments. The reaction was exothermic, and the reaction progress was monitored by tlc 40%EtOAc/Hexane. Additional TFA, $BH_3$ * pyridine and acetal were added until the tlc indicated that the 5-chloro-2-nitroaniline was consumed. The reaction mixture was washed 2X with water and placed on a bed of silica and eluted with toluene. The product was the first major component to elute. The product was crystallized from MeOH which produced 17.6 g (88%) of a yellow crystalline solid.

$C_8H_9ClN_2O_2$ M.W. 200.63.

| Elements | Calc | Found |
|---|---|---|
| Carbon | 47.89 | 47.69 |
| Hydrogen | 4.52 | 4.36 |
| Nitrogen | 13.96 | 13.92 |
| Chlorine | 17.67 | 17.71 |

EXAMPLE 6

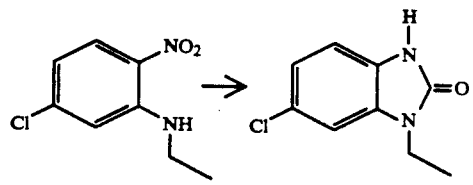

5-chloro-N-ethyl-2-nitroaniline →6-chloro-1-ethyl-

-continued 1,3-dihydro-2H-benzimidazol-2-one 5-chloro-N-ethyl-2-nitroaniline (17.6 g; 0.0877 mole) was dissolved in MeOH (1.0 l) and hydrogenated at room temperature, at 5.0 psi over Ra-Ni for 1.9 hr. at which time the theoretical hydrogen uptake had been achieved. The reaction mixture was filtered and the filtrate was concentrated. The residue was dissolved in CH$_2$Cl$_2$ (500 ml) and triphosgene (8.6 g; 0.029 mole) dissolved in 50 ml of CH$_2$Cl$_2$ was added. The reaction was exothermic. The reaction mixture was stirred for 1 hr. and then concentrated. The solid was triturated with water and filtered, washed with Et$_2$O and suction dried which produced 7.9 g (46%) of a blue-white solid.

C$_9$H$_9$ClN$_2$O M.W. 196.64.

| Elements | Calc | Found |
|---|---|---|
| Carbon | 52.57 | 52.18 |
| Hydrogen | 4.90 | 4.68 |
| Nitrogen | 13.62 | 13.68 |
| Chlorine | 17.24 | 17.17 |

EXAMPLE 7

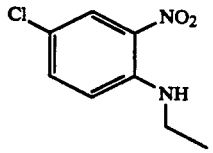

4-chloro-N-ethyl-2-nitroaniline 4-chloro-2-nitroaniline (8.6 g; 0.05 mole), acetaldehyde (5.5 ml; 0.05 mole) and HOAc (4.0 ml; 0.1 moles) were dissolved in toluene (100 ml) and stirred for 1 hr. BH$_3$ * pyridine (5.0 ml; 0.01 moles) was added in 1.0 ml increments. The reaction was exothermic, and the reaction progress was monitored by tlc (40%EtOAc/Hexane). Additional TFA, BH$_3$ * pyridine and acetaldehyde were added until the tlc indicated that the 4-chloro-2-nitroaniline was consumed. The reaction mixture was washed 2X with water and placed on a bed of silica and eluted with 20% EtOAc/Hexane. The product was the first major component to elute. The product was crystallized from MeOH which produced 5.0 g (50%) of a yellow crystalline solid.

C$_8$H$_9$ClN$_2$O$_2$ M.W. 200.63.

| Elements | Calc | Found |
|---|---|---|
| Carbon | 47.89 | 47.57 |
| Hydrogen | 4.52 | 4.41 |
| Nitrogen | 13.96 | 14.07 |
| Chlorine | 17.67 | 17.77 |

EXAMPLE 8

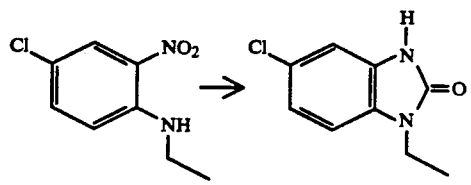

-continued 4-chloro-N-ethyl-2-nitroaniline ⟶ 5-chloro-1-ethyl-1,3-dihydro-2H-benzimidazol-2-one 4-chloro-N-ethyl-2-nitroaniline (8.7 g; 0.0436 mole) was dissolved in MeOH (330 ml) and hydrogenated at room temperature, at 5.0 psi over Ra-Ni for 3.1 hr. at which time the theoretical hydrogen uptake had been achieved. The reaction mixture was filtered and the filtrate was concentrated. The residue was dissolved in CH$_2$Cl$_2$ (200 ml) and triphosgene (4.3 g; 0.0145 mole) dissolved in 25 ml of CH$_2$Cl$_2$ was added. The reaction was exothermic. The reaction mixture was stirred for 1 hr. then concentrated. The solid was triturated with water and filtered, washed with Et$_2$O and suction dried which produced 5.5 g (64%) of a blue-white solid.

C$_9$H$_9$ClN$_2$O M.W. 196.64.

| Elements | Calc | Found |
|---|---|---|
| Carbon | 52.57 | 52.83 |
| Hydrogen | 4.90 | 4.90 |
| Nitrogen | 13.62 | 13.74 |
| Chlorine | 17.24 | 17.21 |

EXAMPLE 9

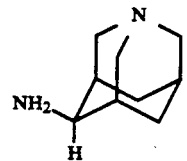

This compound was prepared by the methodology of E. A. Watts, in U.S. Pat. No. 4,816,453 (1989).

EXAMPLE 10

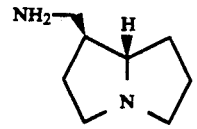

This compound was prepared by the method of D. L. Flynn et al., J. Med. Chem., 35, 1486 (1992).

EXAMPLE 11

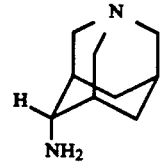

This compound was prepared by the methodology of E. A. Watts, in U.S. Pat. No. 4,816,453 (1989).

EXAMPLE 12

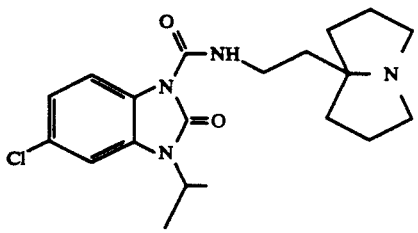

5-chloro-N-[2-(hexahydro-7aH-pyrrolizin-7a-yl)ethyl]-2,3-dihydro-3-(1-methylethyl)-2-oxo-1H-benzimidazole-1-carboxamide 60% NaH/Mineral oil (80 mg; 0.002 mole) was washed with hexane and suspended in THF. 6-chloro-1,3-dihydro-1-(1-methylethyl)-2H-benzimidazol-2-one (105 mg; 0.0005 mole) was added to the suspension. This mixture was stirred 15 minutes before adding to a mixture of 2.5 ml (0.004 mole) 20% phosgene in toluene/2.5 ml THF. The resulting mixture was filtered through celite and concentrated. The residue was dissolved in THF (5.0 ml) and 7a-(2-aminoethyl)hexahydro-1H-pyrrolizine [the Journal of Heterocyclic Chemistry, 24, 271 (1987)) (77 mg; 0.0005 mole) was added with 0.5 ml of Et₃N. This mixture was stirred 1 hr., filtered and the filtrate concentrated. The residue was chromatographed first on a 2 mm Chromatron plate, and the semi-purified fraction containing the product was rechromatographed on a prep tlc plate, in both cases eluting with 20%MeOH/CHCl₃/0.25%NH₄OH. The product was washed from the silica with 5%NH₄OH/MeOH. The filtrate was concentrated and the residue was dissolved in CHCl₃ and filtered through celite and concentrated. 51 mg (26%) of product was isolated. The product was converted to the HCl salt by dissolving 11.1 µl of acetyl chloride in 5.0 ml of MeOH and adding this solution to the product, then concentrating to dryness.

$C_{20}H_{27}ClN_4O_2$ * 1.2 HCl M.W. 437.67.

| Elements | Calc | Found |
|---|---|---|
| Carbon | 55.27 | 55.57 |
| Hydrogen | 6.54 | 6.42 |
| Nitrogen | 12.89 | 12.89 |
| Chlorine | 17.94 | 17.88 |

EXAMPLE 13

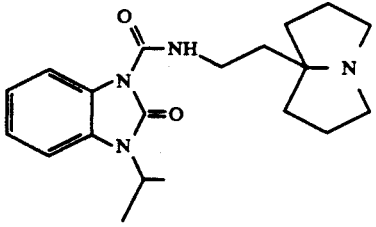

N-[2-(hexahydro-7aH-pyrrolizin-7a-yl)ethyl]-2,3-dihydro-3-(1-methylethyl)-2-oxo-1H-benzimidazole-1-carboxamide 60% NaH/Mineral oil (80 mg; 0.002 mole) was washed with hexane and suspended in THF. 1,3-dihydro-1-(1-methylethyl)-2H-benzimidazol-2-one (176 mg; 0.001 mole) was added to the suspension. This mixture was stirred 15 minutes before adding to a mixture of 2.5 ml (0.004 mole) 20% phosgene in toluene/2.5 ml THF. The resulting mixture was filtered through celite and concentrated. The residue was dissolved in THF (5.0 ml) and 7a-(2-aminoethyl)hexahydro-1H-pyrrolizine (77 mg; 0.0005 mole) was added with 0.5 ml of Et₃N. This mixture was stirred 1 hr., filtered and the filtrate concentrated. The residue was chromatographed on a prep tlc plate, eluting with 20%MeOH/CHCl₃/0.25%NH₄OH. The product was washed from the silica with 5%NH₄OH/MeOH. The filtrate was concentrated and the residue was dissolved in CHCl₃ and filtered through celite and concentrated. 149 mg (83.7%) of product was isolated. The product was converted to the HCl salt by dissolving 35.6 µl of acetyl chloride in 5.0 ml of MeOH and adding this solution to the product, then concentrating to dryness.

$C_{20}H_{28}N_4O_2$ * 1.2 HCl 0.25 H₂O M.W. 437.67.

| Elements | Calc | Found |
|---|---|---|
| Carbon | 59.21 | 58.94 |
| Hydrogen | 7.63 | 7.27 |
| Nitrogen | 13.78 | 13.78 |
| Chlorine | 10.49 | 10.25 |

EXAMPLE 13A

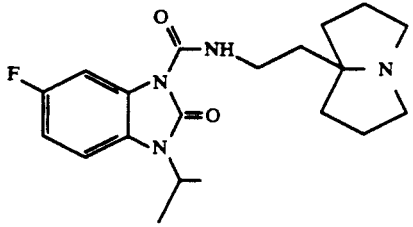

6-fluoro-N-[2-(hexahydro-7aH-pyrrolizin-7a-yl)ethyl]-2,3-dihydro-3-(1-methylethyl)-2-oxo-1H-benzimidazole-1-carboxamide 60% NaH/Mineral oil (80 mg; 0.002) was washed with hexane and suspended in THF. 6-fluoro-1,3-dihydro-1-(1-methylethyl)-2H-benzimidazol-2-one (145 mg; 0.00075 mole) was added to the suspension. This mixture was stirred 15 minutes before adding to a mixture of 2.5 ml (0.004 mole) 20% phosgene in toluene/2.5 ml THF. The resulting mixture was filtered through celite and concentrated. The residue was dissolved in THF (5.0 ml) and 7a-(2-aminoethyl) hexahydro-1H-pyrrolizine [the Journal of Heterocyclic Chemistry, 24, 271 (1987)] (77 mg; 0.0005 mole) was added with 0.5 ml of Et₃N. This mixture was stirred 1 hr., filtered and the filtrate concentrated. The residue was chromatographed first on a 2 mm Chromatron plate, and the semi-purified fraction containing the product was rechromatographed on a prep tlc plate, in both cases eluting with 10%MeOH/CHCl₃/0.25%NH₄OH. The product was washed from the silica with 5%NH₄OH/MeOH. The filtrate was concentrated and the residue was dissolved in CHCl₃ and filtered through celite and concentrated. 105 mg (56%) of product was isolated. The product was converted to the HCl salt by dissolving 11.1 gl of acetyl chloride in 5.0 ml of MeOH and adding this solution to the product, and then concentrating to dryness.

C$_{20}$H$_{27}$FN$_4$O$_2$*1.1 HCl*H$_2$O M.W. 432.58.

| Elements | Calc | Found |
|---|---|---|
| Carbon | 55.53 | 55.62 |
| Hydrogen | 7.01 | 7.01 |
| Nitrogen | 12.95 | 12.91 |
| Chlorine | 9.02 | 9.35 |

EXAMPLE 13B

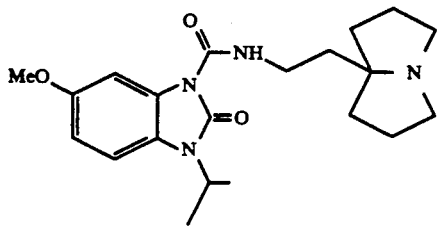

N-[2-(hexahydro-7aH-pyrrolizin-7a-yl)ethyl]-2,3-dihydro-6-methoxy-3-(1-methylethyl)-2-oxo-1H-benzimidazole-1-carboxamide 60% NaH/Mineral oil (8 mg; 0.002) was washed with hexane and suspended in THF. 1,3-dihydro-6-methoxy-1-(1-methylethyl)-2H-benzimidazol-2-one (154 mg; 0.00075 mole) was added to the suspension. This mixture was stirred 15 minutes before adding to a mixture of 2.5 ml (0.004 mole) 20% phosgene in toluene/2.5 ml THF. The resulting mixture was filtered through celite and concentrated. The residue was dissolved in THF (5.0 ml) and 7a-(2-aminoethyl)hexahydro-1H-pyrrolizine [the Journal of Heterocyclic Chemistry, 24, 271 (1987)] (77 mg; 0.0005 mole) was added with 0.5 ml of Et$_3$N. This mixture was stirred 1 hr., filtered and the filtrate concentrated. The residue was chromatographed first on a 2 mm Chromatron plate, and the semi-purified fraction containing the product was re-chromatographed on a prep tlc plate, in both cases eluting with 10% MeOH/CHCl$_3$/0.25%NH$_4$OH. The product was washed from the silica with 5% NH$_4$OH/MeOH. The filtrate was concentrated and the residue was dissolved in CHCl$_3$ and filtered through celite and concentrated. 118 mg (61%) of product was isolated. The product was converted to the HCl salt by dissolving 11.1 μl of acetyl chloride in 5.0 ml of MeOH and adding this solution to the product, then concentrating to dryness.

C$_{21}$H$_{30}$N$_4$O$_3$ HCl * 1.25 H$_2$O M.W. 445.48.

| Elements | Calc | Found |
|---|---|---|
| Carbon | 56.62 | 56.64 |
| Hydrogen | 7.58 | 7.48 |
| Nitrogen | 12.58 | 12.52 |
| Chlorine | 7.96 | 7.74 |

EXAMPLE 13C

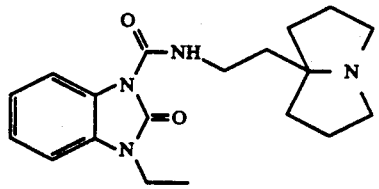

3-ethyl-N-[(hexahydro-7aH-pyrrolizin-7a-yl)ethyl]-2,3-dihydro-2-oxo-1H-benzimidazole-1-carboxamide 60% NaH/Mineral oil (80 mg; 0.002) was washed with hexane and suspended in THF. 1-ethyl-1,3-dihydro-2H-benzimidazol-2-one (121 mg; 0.00075 mole) was added to the suspension. This mixture was stirred 15 minutes before adding to a mixture of 2.5 ml (0.004 mole) 20% phosgene in toluene/2.5 ml THF. The resulting mixture was filtered through celite and concentrated. The residue was dissolved in THF (5.0 ml) and 7a-(2-aninoethyl) hexahydro-1H-pyrrolizine [the Journal of Heterocyclic Chemistry, 24, 271 (1987)] (77 mg; 0.0005 mole) was added with 0.5 μl of Et$_3$N. This mixture was stirred 1 hr., filtered and the filtrate concentrated. The residue was chromatographed on a prep tlc plate, eluting with 10% MeOH/CHCl$_3$/0.25 NH$_4$OH. The product was washed from the silica with 5% NH$_4$OH/MeOH. The filtrate was concentrated and the residue was dissolved in CHCl$_3$ and filtered through celite and concentrated. 147 mg (86%) of product was isolated. The product was converted to the HCl salt by dissolving 16 μl of acetyl chloride in 5.0 ml of MeOH and adding this solution to the product, then concentrating to dryness.

C$_{19}$H$_{26}$N$_4$O$_2$ * 1.25 H$_2$O M.W. 380.53.

| Elements | Calc | Found |
|---|---|---|
| Carbon | 59.97 | 59.69 |
| Hydrogen | 6.65 | 6.52 |
| Nitrogen | 14.72 | 14.67 |
| Chlorine | 10.25 | 10.40 |

EXAMPLE 14

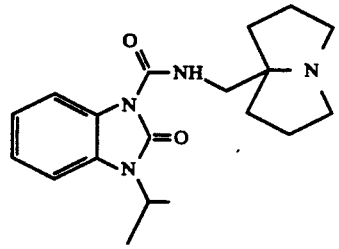

N-[(hexahydro-7aH-pyrrolizin-7a-yl)methyl]-2,3-dihydro-3-(1-methylethyl)-2-oxo-1H-benzimidazole-1-carboxamide 60% NaH/Mineral oil (80 mg; 0.002 mole) was washed with hexane and suspended in THF. 1,3-dihydro-1-(1-methylethyl)-2H-benzimidazol-2-one (176 mg; 0.001 mole) was added to the suspension. This mixture was stirred 15 minutes before adding to a mixture of 2.5 ml (0.004 mole) 20% phosgene in toluene/2.5 ml THF.

The resulting mixture was filtered through celite and concentrated. The residue was dissolved in THF (5.0 ml) and 7a-aminomethylhexahydro-1H-pyrrolizine [the Journal of Heterocyclic Chemistry, 24, 47(1987)] (70 mg; 0.0005 mole) was added with 0.5 ml of Et₃N. This mixture was stirred 1 hr., filtered and the filtrate concentrated. The residue was chromatographed on a prep tlc plate, eluting with 10%MeOH/CHCl₃/0.25%NH₄OH. The product was washed from the silica with 5%NH₄OH/MeOH. The filtrate was concentrated and the residue was dissolved in CHCl₃ and filtered through celite and concentrated. 149 mg (83.7%) of product was isolated. The product was converted to the HCl salt by dissolving 35.6 gl of acetyl chloride in 5.0 ml of MeOH and adding this solution to the product, then concentrating to dryness.

$C_{19}H_{26}N_4O_2$ * 1.15 HCl 0.5 H₂O M.W. 394.39.

| Elements | Calc | Found |
|---|---|---|
| Carbon | 57.86 | 57.88 |
| Hydrogen | 7.45 | 7.07 |
| Nitrogen | 14.21 | 13.83 |
| Chlorine | 10.13 | 10.13 |

EXAMPLE 15

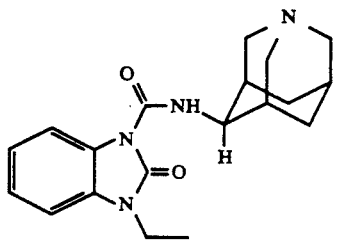

N-(1-azatricyclo[3.3.1.1³,⁷]decan-4-yl)-3-ethyl-2,3-dihydro-2-oxo-1H-benzimidazole-1-carboxamide 60% NaH/Mineral oil (80 mg; 0.002 mole) was washed with hexane and suspended in THF. 1-ethyl-1,3-dihydro-2H-benzimidazol-2-one (121 mg; 0.00075 mole) was added to the suspension. This mixture was stirred 15 minutes before adding to a mixture of 2.5 ml (0.004 mole) 20% phosgene in toluene/2.5 ml THF. The resulting mixture was filtered through celite and concentrated. The residue was dissolved in THF (5.0 ml) and the compound prepared in Example 9 (104 mg; 0.00075 mole) was added with 0.5 ml of Et₃N. This mixture was stirred 1 hr., filtered and the filtrate concentrated. The residue was chromatographed on a prep tlc plate, eluting with 10%MeOH/CHCl₃/0.25 NH₄OH. The product was washed from the silica with 5%NH₄OH/MeOH. The filtrate was concentrated and the residue was dissolved in CHCl₃ and filtered through celite and concentrated. 184 mg (74%) of product was isolated. The product was converted to the HCl salt by dissolving 16 μl of acetyl chloride in 5.0 ml of MeOH and adding this solution to the product, then concentrating to dryness.

$C_{19}H_{24}N_4O_2$ * 1.1 HCl M.W. 380.53.

| Elements | Calc | Found |
|---|---|---|
| Carbon | 59.97 | 59.69 |
| Hydrogen | 6.65 | 6.52 |
| Nitrogen | 14.72 | 14.67 |
| Chlorine | 10.25 | 10.40 |

EXAMPLE 16

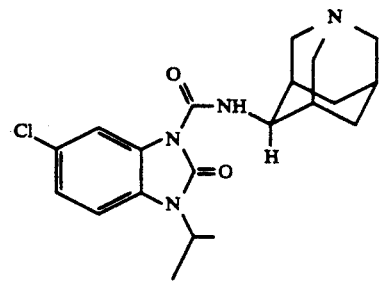

N-(1-azatricyclo[3.3.1.1³,⁷]decan-4-yl)-6-chloro-2,3-dihydro-3-(1-methylethyl)-2-oxo-1H-benzimidazole-1-carboxamide 60% NaH/Mineral oil (80 mg; 0.002 mole) was washed with hexane and suspended in THF. 5-chloro-1,3-dihydro-1-(1-methylethyl)-2H-benzimidazol-2-one (157 mg; 0.00075 mole) was added to the suspension. This mixture was stirred 15 minutes before adding to a mixture of 2.5 ml (0.004 mole) 20% phosgene in toluene/2.5 ml THF. The resulting mixture was filtered through celite and concentrated. The residue was dissolved in THF (5.0 ml) and the compound prepared in Example 9 (104 mg; 0.00075 mole) was added with 0.5 ml of Et₃N. This mixture was stirred 1 hr., filtered and the filtrate concentrated. The residue was chromatographed on a prep tlc plate, eluting with 10%MeOH/CHCl₃/0.25%NH₄OH. The product was washed from the silica with 5%NH₄OH/MeOH. The filtrate was concentrated and the residue was dissolved in CHCl₃ and filtered through celite and concentrated. 184 mg (74%) of product was isolated. The product was converted to the HCl salt by dissolving 26 μl of acetyl chloride in 5.0 ml of MeOH and adding this solution to the product, then concentrating to dryness.

$C_{20}N_{25}ClN_4O_2$ * 1.05 HCl 0.5 H₂O M.W. 436.19.

| Elements | Calc | Found |
|---|---|---|
| Carbon | 55.07 | 55.27 |
| Hydrogen | 6.25 | 5.98 |
| Nitrogen | 12.84 | 12.85 |
| Chlorine | 16.66 | 16.87 |

EXAMPLE 17

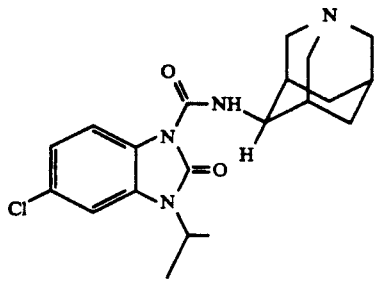

N-(1-azatricyclo[3.3.1.1³,⁷]decan-4-yl)-5-chloro-2,3-dihydro-

-continued 3-(1-methylethyl)-2-oxo-1H-benzimidazole-1-carboxamide

60% NaH/Mineral oil (80 mg; 0.002 mole) was washed with hexane and suspended in THF. 6-chloro-1,3-dihydro-1-(1-methylethyl)-2H-benzimidazol-2-one (157 mg; 0.00075 mole) was added to the suspension. This mixture was stirred 15 minutes before adding to a mixture of 2.5 ml (0.004 mole) 20% phosgene in toluene/2.5 ml THF. The resulting mixture was filtered through celite and concentrated. The residue was dissolved in THF (5.0 ml) and the compound prepared in Example 9 (104 mg; 0.00075 mole) was added with 0.5 ml of Et$_3$N. This mixture was stirred 1 hr., filtered and the filtrate concentrated. The residue was chromatographed on a prep tlc plate, eluting with 10%MeOH/CHCl$_3$/0.25%NH$_4$OH. The product was washed from the silica with 5%NH$_4$OH/MeOH. The filtrate was concentrated and the residue was dissolved in CHCl$_3$ and filtered through celite and concentrated. 150 mg (53%) of product was isolated. The product was converted to the HCl salt by dissolving 30 μl of acetyl chloride in 5.0 ml of MeOH and adding this solution to the product, then concentrating to dryness.

$C_{20}H_{25}ClN_4O_2$ * HCl H$_2$O M.W. 443.38.

| Elements | Calc | Found |
|---|---|---|
| Carbon | 54.18 | 54.38 |
| Hydrogen | 6.37 | 6.06 |
| Nitrogen | 12.64 | 12.66 |
| Chlorine | 15.99 | 16.27 |

EXAMPLE 18

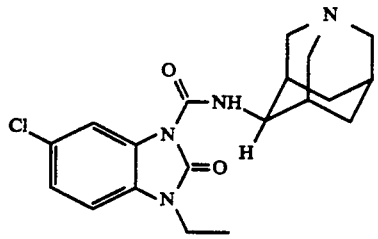

N-(1-azatricyclo[3.3.1.1$^{3,7}$]decan-4-yl)-6-chloro-3-ethyl-2,3-dihydro-2-oxo-1H-benzimidazole-1-carboxamide 60% NaH/Mineral oil (80 mg; 0.002 mole) was washed with hexane and suspended in THF. 5-chloro-1-ethyl-1,3-dihydro-2H-benzimidazol-2-one (147 mg; 0.00075 mole) was added to the suspension. This mixture was stirred 15 minutes before adding to a mixture of 2.5 ml (0.004 mole) 20% phosgene in toluene/2.5 ml THF. The resulting mixture was filtered through celite and concentrated. The residue was dissolved in THF (5.0 ml) and the compound prepared in Example 9 (104 mg; 0.00075 mole) was added with 0.5 ml of Et$_3$N. This mixture was stirred 1 hr., filtered and the filtrate concentrated. The residue was chromatographed on a prep tlc plate, eluting with 10%MeOH/CHCl$_3$/0.25%NH$_4$OH. The product was washed from the silica with 5%NH$_4$OH/MeOH. The filtrate was concentrated and the residue was dissolved in CHCl$_3$ and filtered through celite and concentrated. 200 mg (73%) of product was isolated. The product was converted to the HCl salt by dissolving 42 μl of acetyl chloride in 5.0 ml of MeOH and adding this solution to the product, then concentrating to dryness.

$C_{19}H_{23}ClN_4O_2$ * HCl * 0.75 M.W. 422.05.

| Elements | Calc | Found |
|---|---|---|
| Carbon | 54.07 | 54.26 |
| Hydrogen | 5.83 | 5.83 |
| Nitrogen | 13.27 | 13.24 |
| Chlorine | 15.12 | 15.15 |

EXAMPLE 19

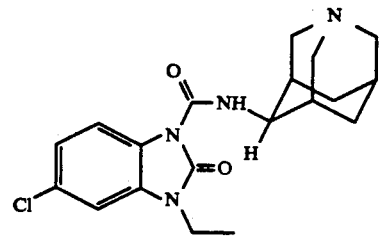

N-(1-azatricyclo[3.3.1.1$^{3,7}$]decan-4-yl)-5-chloro-3-ethyl-2,3-dihydro-2-oxo-1H-benzimidazole-1-carboxamide 60% NaH/Mineral oil (80 mg; 0.002 mole) was washed with hexane and suspended in THF. 6-chloro-1-ethyl-1,3-dihydro-2H-benzimidazol-2-one (147 mg; 0.00075 mole) was added to the suspension. This mixture was stirred 15 minutes before adding to a mixture of 2.5 ml (0.004 mole) 20% phosgene in toluene/2.5 ml THF. The resulting mixture was filtered through celite and concentrated. The residue was dissolved in THF (5.0 ml) and the compound prepared in Example 9 (104 mg; 0.00075 mole) was added with 0.5 ml of Et$_3$N. This mixture was stirred 1 hr., filtered and the filtrate concentrated. The residue was chromatographed on a prep tlc plate, eluting with 10%MeOH/CHCl$_3$/0.25%NH$_4$OH. The product was washed from the silica with 5%NH$_4$OH/MeOH. The filtrate was concentrated and the residue was dissolved in CHCl$_3$ and filtered through celite and concentrated. 181 mg (66%) of product was isolated. The product was converted to the HCl salt by dissolving 38 μl of acetyl chloride in 5.0 ml of MeOH and adding this solution to the product, then concentrating to dryness.

$C_{19}H_{23}ClN_4O_2$ * 0.9 HCl * H$_2$O M.W. 425.70.

| Elements | Calc | Found |
|---|---|---|
| Carbon | 53.61 | 53.79 |
| Hydrogen | 5.75 | 5.75 |
| Nitrogen | 13.16 | 13.11 |
| Chlorine | 15.82 | 15.54 |

EXAMPLE 19A

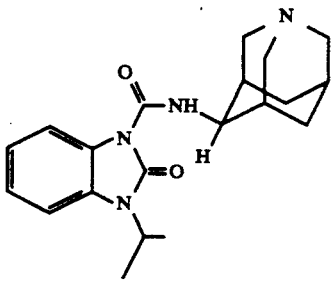

N-(1-azatricyclo[3.3.1.1^{3,7}]decan-4-yl)-2,3-dihydro-3-(1-methylethyl)-2-oxo-1H-benzimidazole-1-carboxamide 60% NaH/Mineral oil (80 mg; 0.002) was washed with hexane and suspended in THF. 1,3-dihydro-1-(1-methylethyl)-2H-benzimidazol-2-one (132 mg; 0.00075 mole) was added to the suspension. This mixture was stirred 15 minutes before adding to a mixture of 2.5 ml (0.004 mole) 20% phosgene in toluene/2.5 ml THF. The resulting mixture was filtered through celite and concentrated. The residue was dissolved in THF (5.0 ml) and the compound prepared in example 9 (104 mg; 0.00075 mole) was added with 0.5 ml of Et$_3$N. This mixture was stirred 1 hr., filtered and the filtrate concentrated. The residue was chromatographed on a prep tlc plate, eluting with 10% MeOH/CHCl$_3$/0.25 NH$_4$OH. The product was washed from the silica with 5% NH$_4$OH/MeOH. The filtrate was concentrated and the residue was dissolved in CHCl$_3$ and filtered through celite and concentrated. 118 mg (46%) of product was isolated. The product was converted to the HCl salt by dissolving 16 μl of acetyl chloride in 5.0 ml of MeOH and adding this solution to the product, then concentrating to dryness.

$C_{20}H_{26}N_4O_2$ * 1.1 HCl * 1.25 H$_2$O M.W. 417.08.

| Elements | Calc | Found |
| --- | --- | --- |
| Carbon | 57.60 | 57.92 |
| Hydrogen | 7.15 | 6.88 |
| Nitrogen | 13.43 | 13.39 |
| Chlorine | 9.35 | 9.26 |

EXAMPLE 20

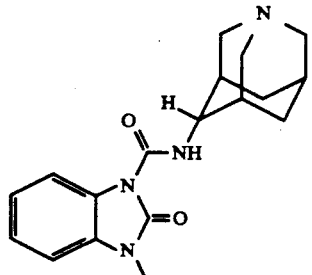

N-(1-azatricyclo[3.3.1.1^{3,7}]decan-4-yl)-3-ethyl-2,3-dihydro-2-oxo-1H-benzimidazole-1-carboxamide 60% NaH/Mineral oil (80 mg; 0.002 mole) was washed with hexane and suspended in THF. 1-ethyl-1,3-dihydro-2H-benzimidazol-2-one (121 mg; 0.00075 mole) was added to the suspension. This mixture was stirred 15 minutes before adding to a mixture of 2.5 ml (0.004 mole) 20% phosgene in toluene/2.5 ml THF. The resulting mixture was filtered through celite and concentrated. The residue was dissolved in THF (5.0 ml) and the compound prepared in Example 11 (104 mg; 0.00075 mole) was added with 0.5 ml of Et$_3$N. This mixture was stirred 1 hr. filtered and the filtrate concentrated. The residue was chromatographed on a prep tlc plate, eluting with 10%MeOH/CHCl$_3$/0.25%NH$_4$OH. The product was washed from the silica with 5%NH$_4$OH/MeOH. The filtrate was concentrated and the residue was dissolved in CHCl$_3$ and filtered through celite and concentrated. 160 mg (64.5%) of product was isolated. The product was converted to the HCl salt by dissolving 36 μl of acetyl chloride in 5.0 ml of MeOH and adding this solution to the product, then concentrating to dryness.

$C_{19}N_{24}N_4O_2$ * 1.1 HCl * 1.25 H$_2$O M.W. 403.05.

| Elements | Calc | Found |
| --- | --- | --- |
| Carbon | 56.62 | 56.40 |
| Hydrogen | 6.90 | 6.71 |
| Nitrogen | 13.90 | 13.70 |
| Chlorine | 9.68 | 9.34 |

EXAMPLE 21

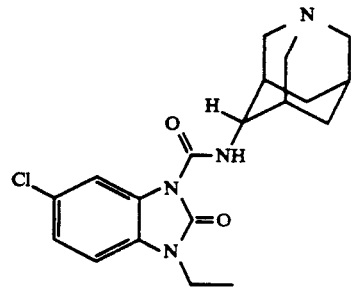

N-(1-azatricyclo[3.3.1.1^{3,7}]decan-4-yl)-6-chloro-3-ethyl-2,3-dihydro-2-oxo-1H-benzimidazole-1-carboxamide 60% NaH/Mineral oil (80 mg; 0.002 mole) was washed with hexane and suspended in THF. 5-chloro-1,3-dihydro-1-ethyl-2H-benzimidazol-2-one (147 mg; 0.00075 mole) was added to the suspension. This mixture was stirred 15 minutes before adding to a mixture of 2.5 ml (0.004 mole) 20% phosgene in toluene/2.5 ml THF. The resulting mixture was filtered through celite and concentrated. The residue was dissolved in THF (5.0 ml) and the compound prepared in Example 11 (104 mg; 0.00075 mole) was added with 0.5 ml of Et$_3$N. This mixture was stirred 1 hr., filtered and the filtrate concentrated. The residue was chromatographed on a prep tlc plate, eluting with 10%MeOH/CHCl$_3$/0.25%NH$_4$OH. The product was washed from the silica with 5%NH$_4$OH/MeOH. The filtrate was concentrated and the residue was dissolved in CHCl$_3$ and filtered through celite and concentrated. 149 mg (54%) of product was isolated. The product was converted to the HCl salt by dissolving 31 μl of acetyl chloride in 5.0 ml of MeOH and adding this solution to the product, then concentrating to dryness.

$C_{19}H_{23}ClN_4O_2$ * HCl H$_2$O 0.75 MeOH M.W. 453.38.

| Elements | Calc | Found |
|---|---|---|
| Carbon | 52.32 | 52.69 |
| Hydrogen | 6.45 | 6.18 |
| Nitrogen | 12.36 | 12.36 |
| Chlorine | 15.64 | 15.42 |

EXAMPLE 22

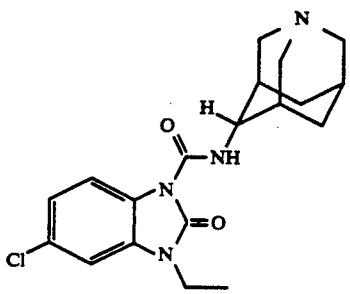

N-(1-azatricyclo[3.3.1.1³,⁷]decan-4-yl)-5-chloro-3-ethyl-2,3-dihydro-2-oxo-1H-benzimidazole-1-carboxamide 60% NaH/Mineral oil (80 mg; 0.002 mole) was washed with hexane and suspended in THF. 6-chloro-1-ethyl-1,3-dihydro-2H-benzimidazol-2-one (147 mg; 0.00075 mole) was added to the suspension. This mixture was stirred 15 minutes before adding to a mixture of 2.5 ml (0.004 mole) 20% phosgene in toluene/2.5 ml THF. The resulting mixture was filtered through celite and concentrated. The residue was dissolved in THF (5.0 ml) and the compound prepared in Example 11 (104 mg; 0.00075 mole) was added with 0.5 ml of Et₃N. This mixture was stirred 1 hr., filtered and the filtrate concentrated. The residue was chromatographed on a prep tlc plate, eluting with 10%MeOH/CHCl₃/0.25%NH₄OH. The product was washed from the silica with 5%NH₄OH/MeOH. The filtrate was concentrated and the residue was dissolved in CHCl₃ and filtered through celite and concentrated. 186 mg (68%) of product was isolated. The product was converted to the HCl salt by dissolving 39 μl of acetyl chloride in 5.0 ml of MeOH and adding this solution to the product, then concentrating to dryness.

$C_{19}H_{23}ClN_4O_2$ * HCl * H₂O M.W. 429.35.

| Elements | Calc | Found |
|---|---|---|
| Carbon | 53.15 | 53.18 |
| Hydrogen | 6.10 | 5.79 |
| Nitrogen | 13.05 | 12.93 |
| Chlorine | 16.51 | 16.16 |

EXAMPLE 22A

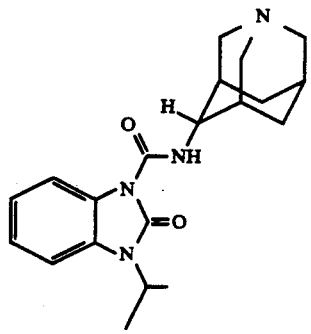

N-(1-azatricyclo[3.3.1.1³,⁷]decan-4-yl)-2,3-dihydro-3-(1-methylethyl)-2-oxo-1H-benzimidazole-1-carboxamide 60% NaH/Mineral oil (80 mg; 0.002) was washed with hexane and suspended in THF. 1,3-dihydro-1-(1-methylethyl)-2H-benzimidazol-2-one (132 mg; 0.00075 mole) was added to the suspension. This mixture was stirred 15 minutes before adding to a mixture of 2.5 ml (0.004 mole) 20% phosgene in toluene/2.5 ml THF. The resulting mixture was filtered through celite and concentrated. The residue was dissolved in THF (5.0 ml) and the compound prepared in Example 11 (104 mg; 0.00075 mole) was added with 0.5 ml of Et₃N. This mixture was stirred 1 hr., filtered and the filtrate concentrated. The residue was chromatographed on a prep tlc plate, eluting with 10% MeOH/CHCl₃/0.25 NH₄OH. The product was washed from the silica with 5% NH₄OH/MeOH. The filtrate was concentrated and the residue was dissolved in CHCl₃ and filtered through celite and concentrated. 194 mg (75%) of product was isolated. The product was converted to the HCl salt by dissolving 16 μl of acetyl chloride in 5.0 ml of MeOH and adding this solution to the product and then concentrating to dryness.

$C_{20}H_{26}N_4O_2$ * 1.5 HCl * 1.75 H₂O M.W. 440.67.

| Elements | Calc | Found |
|---|---|---|
| Carbon | 54.51 | 54.41 |
| Hydrogen | 7.09 | 6.98 |
| Nitrogen | 12.71 | 12.47 |
| Chlorine | 12.07 | 11.76 |

EXAMPLE 22B

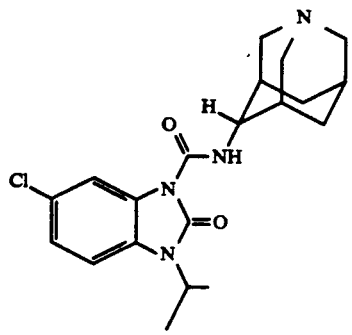

N-(1-azatricyclo[3.3.1.1³,⁷]decan-4-yl)-6-chloro-2,3-dihydro-3-(1-methylethyl)-2-oxo-1H-benzimidazole-1-carboxamide 60% NaH/Mineral oil (80 mg; 0.002) was washed with hexane and suspended in THF. 5-chloro-1,3-dihydro-1-(1-methylethyl)-2H-benzimidazol-2-one (157 mg; 0.00075 mole) was added to the suspension. This mixture was stirred 15 minutes before adding to a mixture of 2.5 ml (0.004 mole) 20% phosgene in toluene/2.5 ml THF. The resulting mixture was filtered through celite and concentrated. The residue was dissolved in THF (5.0 ml) and the compound prepared in Example 11 (104 mg; 0.00075 mole) was added with 0.5 ml of Et₃N. This mixture was stirred 1 hr., filtered and the filtrate concentrated. The residue was chromatographed on a prep tlc plate, eluting with 10% MeOH/CHCl₃/0.25 NH₄OH. The product was washed from the silica with 5% NH₄OH/MeOH. The filtrate was concentrated and the residue was dissolved in CHCl₃ and filtered through celite and concentrated. 214 mg (76%) of product was isolated. The product was converted to the HCl salt by dissolving 26 μl of acetyl chloride in 5.0 ml of MeOH and adding this solution to the product and then concentrating to dryness.

$C_{20}H_{25}ClN_4O_2$ * 1.2 HCl * 2 H₂O M.W. 468.68.

| Elements | Calc | Found |
|---|---|---|
| Carbon | 51.25 | 51.19 |
| Hydrogen | 6.49 | 6.13 |
| Nitrogen | 11.95 | 11.85 |
| Chlorine | 16.64 | 16.61 |

EXAMPLE 23

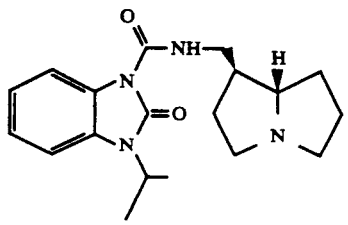

cis-N-[(hexahydro-1H-pyrrolizin-1-yl)methyl]-2,3-dihydro-3-(1-methylethyl)-2-oxo-1H-benzimidazole-1-carboxamide 60% NaH/Mineral oil (80 mg; 0.002 mole) was washed with hexane and suspended in THF. 1,3-dihydro-1-(1-methylethyl)-2H-benzimidazol-2-one (176 mg; 0.001 mole) was added to the suspension. This mixture was stirred 15 minutes before adding to a mixture of 2.5 ml (0.004 mole) 20% phosgene in toluene/2.5 ml THF. The resulting mixture was filtered through celite and concentrated. The residue was dissolved in THF (5.0 ml) and the compound prepared in Example 10 (140 mg; 0.001 mole) was added with 0.5 ml of Et₃N. This mixture was stirred 1 hr., filtered and the filtrate concentrated. The residue was chromatographed on a prep tlc plate, eluting with 30%MeOH/CHCl₃/0.25%NH₄OH. The product was washed from the silica with 5%NH₄OH/MeOH. The filtrate was concentrated and the residue was dissolved in CHCl₃ and filtered through celite and concentrated. 157 mg (50%) of product was isolated. The product was converted to the HCl salt by dissolving 36 μl of acetyl chloride in 5.0 ml of MeOH and adding this solution to the product, then concentrating to dryness.

$C_{19}N_{26}N_4O_2$ * HCl * H₂O M.W. 396.92.

| Elements | Calc | Found |
|---|---|---|
| Carbon | 57.50 | 57.44 |
| Hydrogen | 7.32 | 7.42 |
| Nitrogen | 14.12 | 13.87 |
| Chlorine | 8.93 | 8.93 |

EXAMPLE 24

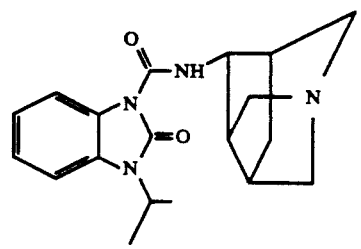

N-(hexahydro-1H-2,5β-methano-3aα,6aα-cyclopenta[c]pyrrol-4α-yl)-2,3-dihydro-3-(1-methylethyl)-2-oxo-1H-benzimidazole-1-carboxamide 60% NaH/Mineral oil (80 mg; 0.002 mole) was washed with hexane and suspended in THF. 1,3-dihydro-1-(1-methylethyl)-2H-benzimidazol-2-one (132 mg; 0.00075 mole) was added to the suspension. This mixture was stirred 15 minutes before adding to a mixture of 2.5 ml (0.004 mole) 20% phosgene in toluene/2.5 ml THF. The resulting mixture was filtered through celite and concentrated. The residue was dissolved in THF (5.0 ml) and N-(hexahydro-1H-2,5β-methano-3aα,6aα-cyclopenta[c]pyrrol-4α-yl)amine (80 mg; 0.000578 mole) [prepared according to method of Becker et al., EP 454,121) was added with 0.5 ml of Et₃N. This mixture was stirred 1 hr., filtered and the filtrate concentrated. The residue was chromatographed on a prep tlc plate, eluting with 10%MeOH/CHCl₃/0.25 NH₄OH. The product was washed from the silica with 5%NH₄OH/MeOH. The filtrate was concentrated and the residue was dissolved in CHCl₃ and filtered through celite and concentrated. 115 mg (59%) of product was isolated. The product was converted to the HCl salt by dissolving 16 μl of acetyl chloride in 5.0 ml of MeOH and adding this solution to the product, then concentrating to dryness.

$C_{19}H_{24}N_4O_2$ * 1 HCl * 1 H₂O M.W. 394.90.

| Elements | Calc | Found |
|---|---|---|
| Carbon | 57.79 | 57.89 |
| Hydrogen | 6.89 | 6.62 |
| Nitrogen | 14.19 | 14.07 |
| Chlorine | 8.98 | 9.06 |

EXAMPLE 25

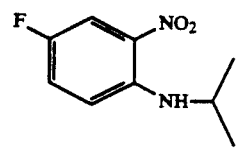

4-fluoro-N-isopropyl-2-nitroaniline 4-fluoro-2-nitroaniline (15.6 g; 0.1 mole), 2,2-dimethoxypropane (24.6 ml; 0.2 mole) and trifluoroacetic acid [TFA] (23.1 ml; 0.005 moles) were dissolved in toluene (500 ml) and stirred for 1 hr. BH$_3$ * pyridine (10.0 ml; 0.1 moles) was added in 1.0 ml increments. The reaction was exothermic, and the reaction progress was monitored by tlc 40% EtOAc/Hexane. Additional TFA, BH$_3$ * pyridine and 2,2-dimethoxypropane were added until the tlc indicated that the 4-fluoro-2-nitroaniline was consumed. The reaction mixture was placed on a bed of silica and eluted with 10% methyl-t-butylether/hexane. The product was the first major component to elute, which produced 11.2 g (58%) of a yellow oil.

$C_9H_{10}FN_2O_2$ M.W. 198.19.

| Elements | Calc | Found |
|---|---|---|
| Carbon | 54.54 | 55.09 |
| Hydrogen | 5.59 | 5.63 |
| Nitrogen | 14.13 | 14.00 |

EXAMPLE 26

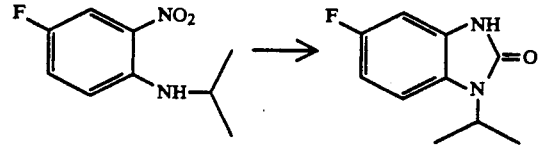

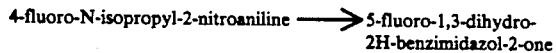

4-fluoro-N-isopropyl-2-nitroaniline ⟶ 5-fluoro-1,3-dihydro-2H-benzimidazol-2-one 4-fluoro-N-isopropyl-2-nitroaniline (11.1 g; 0.0564 mole) was dissolved in MeOH (330 ml) and hydrogenated at room temperature, at 5.0 psi over Ra-Ni for 1.5 hr. at which time the theoretical hydrogen uptake had been achieved. The reaction mixture was filtered and the filtrate was concentrated. The residue was dissolved in CH$_2$Cl$_2$ (200 ml) and triphosgene (5.6 g; 0.0566 mole) dissolved in 25 ml CH$_2$Cl$_2$ was added. The reaction was exothermic. The reaction mixture was stirred for 1 hr. and then concentrated. The solid was triturated with water and filtered, washed with Et$_2$O and suction dried. 5.2 g (47.5%) of a purple-white solid.

$C_{10}H_{11}FN_2O$ * 0.1 H$_2$O M.W. 197.8.

| Elements | Calc | Found |
|---|---|---|
| Carbon | 61.28 | 61.06 |
| Hydrogen | 5.76 | 5.52 |
| Nitrogen | 14.29 | 14.22 |

EXAMPLE 27

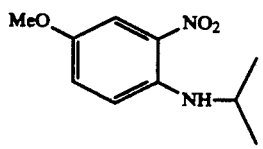

N-isopropyl-4-methoxy-2-nitroaniline 4-methoxy-2-nitroaniline (16.8 g; 0.1 mole), 2,2-dimethoxypropane (24.6 ml; 0.2 mole) and trifluoroacetic acid [TFA] (23.1 ml; 0.005 moles) were dissolved in toluene (500 ml) and stirred for 1 hr. BH$_3$ * pyridine (10.0 ml; 0.1 moles) was added in 1.0 ml increments. The reaction was exothermic, and the reaction progress was monitored by tlc 40% EtOAc/Hexane. Additional TFA, BH$_3$ * pyridine and 2,2-dimethoxypropane were added until the tlc indicated that the 4-fluoro-2-nitroaniline was consumed. The reaction mixture was placed on a bed of silica and eluted with 10% methyl-t-butylether/hexane. The product was the first major component to elute, which produced 13.2 g (62%) of a yellow solid.

$C_{10}H_{14}N_2O_3$ M.W. 210.22.

| Elements | Calc | Found |
|---|---|---|
| Carbon | 57.13 | 57.15 |
| Hydrogen | 6.71 | 6.78 |
| Nitrogen | 13.32 | 13.33 |

EXAMPLE 28

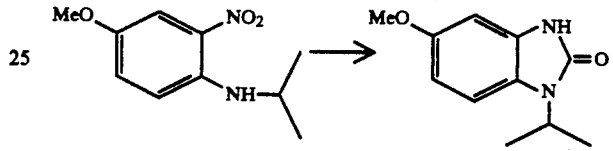

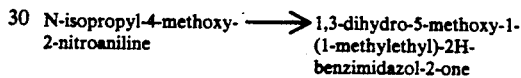

N-isopropyl-4-methoxy-2-nitroaniline ⟶ 1,3-dihydro-5-methoxy-1-(1-methylethyl)-2H-benzimidazol-2-one N-isopropyl-4-methoxy-2-nitroaniline (13.1 g; 0.0627 mole) was dissolved in MeOH (330 ml) and hydrogenated at room temperature, at 5.0 psi over Ra-Ni for 1.5 hr. at which time the theoretical hydrogen uptake had been achieved. The reaction mixture was filtered and the filtrate was concentrated. The residue was dissolved in CH$_2$Cl$_2$ (250 ml) and triphosgene (6.3 g; 0.06447 mole) dissolved in 25 ml CH$_2$Cl$_2$ was added. The reaction was exothermic. The reaction mixture was stirred for 1 hr. then concentrated. The solid was triturated with water and filtered, washed with Et$_2$O and suction dried. 9.9 g (76%) of a purple-white solid.

$C_{11}H_{14}N_2O_2$ * 0.1 H$_2$O M.W. 208.05.

| Elements | Calc | Found |
|---|---|---|
| Carbon | 63.51 | 63.31 |
| Hydrogen | 6.88 | 6.93 |
| Nitrogen | 13.46 | 13.42 |

The benzimidazolone compounds of Examples 26 and 28 can be used to prepare the compounds of the claimed invention in a manner similar to that of Examples 12-24.

BEZOLD-JARISCH REFLEX

The compound to be evaluated was administered i.p. (mg/kg) to a group of 3 mice. Thirty minutes later, a 5-HT (0.25 mg/kg i.v.)-induced bradycardia was recorded in pentobarbital anesthetized animals. A greater than 50 percent (>50) reduction in the bradycardic response relative to vehicle-treated control mice was considered significant.

This method has been described by Saxena, P. R. and Lawang, A., Arch. Int. Pharmacodyn., 277:235-252, 1985.

The assay results for the compounds of the present invention and their Minimum Effective Dose (MED) and the reference compounds and their MEDs are recorded in Table I.

TABLE I

| COMPOUND | Minimum Effective Dose (MED) mg/kg |
|---|---|
| Example 13 | 10 |
| Example 23 | 1 |
| BRL-43694 | 0.05 |
| cisapride | 5 |
| cyproheptadine | 5 |
| domperidone | >10 |
| GR-38032 | 0.5 |
| ketanserin | >10 |
| mecamylamine | 2.5 |
| methylsergide | >10 |
| metoclopramide | 5 |
| scopolamine | 2.5 |

SEROTONIN (5-HT$_3$)

Procedure

GR65630 binds to the 5-HT$_3$ receptor. Brain cortices were obtained from male rats and a membrane fraction prepared by standard techniques. 0.04 mg of membrane prep was incubated with 0.2 nM [$^3$H]-GR656630 for 60 minutes at 22° C. Non-specific binding was estimated in the presence of 1 uM ICS 205-930. Membranes were filtered and washed 3 times and the filters were counted to determine [$^3$H]-GR65630 specifically bound. Kilpatrick G. J., Jones B. J. and Tyers M. B. Identification and distribution of 5-HT$_3$ receptors in rat brain using radioligand binding assay. Nature, 330: 746–748, 1987.

Results
Kd=2.46 nM
Bmax=154 fmol/mg protein
% Specific Binding: 70

TABLE II

| Effect of Compounds on [H]-GR65630 Bound (0.2 nM) | |
|---|---|
| Compound | Ki |
| Quipazine | 0.18 nM |
| ICS 205-930 | 0.51 nM |
| 5-HT | 0.39 uM |
| RU24969 | 1.85 uM |
| Zacopride | 0.18 nM |
| Example 12 | 2,800 nM |
| Example 13 | 120 nM |
| Example 14 | 36 nM |
| Example 15 | 92 nM |
| Example 16 | 1,200 nM |
| Example 17 | 41% @ 10,000 nM |
| Example 18 | 1,200 nM |
| Example 19 | 1,200 nM |
| Example 20 | 19 nM |
| Example 21 | 55 nM |
| Example 22 | 360 nM |
| Example 22B | 4.9 nM |
| Example 23 | 75 nM |
| Example 24 | 2.0 nM |

IN VITRO FUNCTIONAL ASSAY FOR SEROTONIN 5-HT$_4$ AGONISM: RAT TMM

Serotonin 5-HT$_4$ agonism was measured in the rat esophagus in vitro preparation as reported by Baxter et al (Naunyn. Schmied. Arch. Pharmacol. 1991, 343, 439). Agonist activity was determined utilizing relaxation of carbachol-contracted rat tunica muscularis mucosas. One 2 cm segment of intrathoracic esophagus proximal to the diaphragm was removed from male rats, weighing approximately 300 gm, and the outer muscle layers removed. The inner tunica muscularis mucosa was mounted under 0.2–0.3 g of tension in a tissue bath containing oxygenated Tyrodets solution at 37° C. Cortisterone acetate (30 μM) and fluoxetine (1 μM) were included in the buffer to prevent uptake of serotonin, as well as pargyline (10 μM) to inhibit monoamine oxidase. Following a 30 min equilibrium period, tissues were isometrically contracted with carbachol (3 μM) to obtain a tonic contraction. A stable plateau was obtained within 20 min when test compound was added cumulatively to relax the muscle strip. EC50 values were obtained for each agonist in tissues from 5 rats. EC50 values for agonists at this 5-HT$_4$ receptor are indicated in Table III.

TABLE III

| Compound | 5-HT$_4$ Agonism (Rat TMM) In Vitro Assay: EC50 Values |
|---|---|
| Serotonin | 9 nM |
| Example 12 | 9467 nM |
| Example 13 | 179 nM |
| Example 14 | 3833 nM |
| Example 15 | 4584 nM |
| Example 16 | 10000 nM |
| Example 20 | 10000 nM |
| Example 21 | 2135 nM |
| Example 23 | 374 nM |
| Example 24 | 1506 nM |

Although this invention has been described with respect to specific embodiments, the details of these embodiments are not to be construed as limitations. Various equivalents, changes and modifications may be made without departing from the spirit and scope of this invention, and it is understood that such equivalent embodiments are part of this invention.

What is claimed is:

1. A compound of the formula

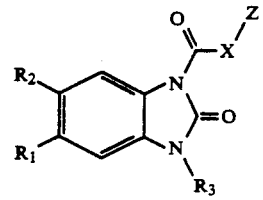

or a pharmaceutically acceptable salt thereof
wherein R$_1$ and R$_2$ are independently selected from the group consisting of hydrogen, alkoxy, halogen, amino, monoalkylamino, dialkylamino, acylamino and alkylsulfonylamino;
R$_3$ is selected from the group consisting of H, alkyl and cycloalkyl;
X is NH or O;
Z is selected from the group consisting of

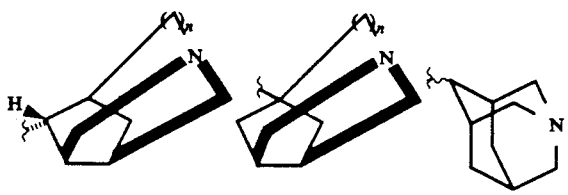

n is 1 or 2.

2. A compound according to claim 1 wherein Z is

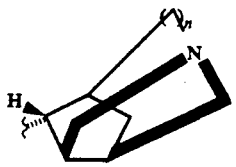

3. A compound according to claim 2 wherein X is NH.

4. A compound according to claim 3 which is N-(hexahydro-1H-2,5β-methano-3aα,6aα-cyclopenta[c]pyrrol-4a-yl)-2,3-dihydro-3-(1-methylethyl)-2-oxo-1H-benzimidazole-1-carboxamide.

5. A compound according to claim 1 wherein Z is

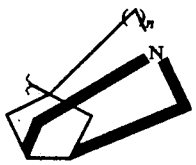

6. A compound according to claim 5 wherein X is NH.

7. A compound according to claim 1 wherein Z is

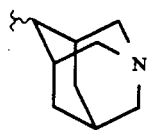

8. A compound according to claim 7 wherein X is NH.

9. A compound according to claim 8 which is endo-N-(1-azatricyclo[3.3.1.1$^{3,7}$]decan-4-yl)-3-ethyl-2,3-dihydro-2-oxo-1H-benzimidazole-1-carboxamide.

10. A compound according to claim 8 which is endo-N-(1-azatricyclo[3.3.1.1$^{3,7}$]decan-4-yl)-6-chloro-2,3-dihydro-3-(1-methylethyl)-2-oxo-1H-benzimidazole-1-carboxamide.

11. A compound according to claim 8 which is endo-N-(1-azatricyclo[3.3.1.1$^{3,7}$]decan-4-yl)-5-chloro-2,3-dihydro-3-(1-methylethyl)-2-oxo-1H-benzimidazole-1-carboxamide.

12. A compound according to claim 8 which is endo-N-(1-azatricyclo[3.3.1.1$^{3,7}$]decan-4-yl)-6-chloro-3-ethyl-2,3-dihydro-2-oxo-1H-benzimidazole-1-carboxamide.

13. A compound according to claim 8 which is endo-N-(1-azatricyclo[3.3.1.1$^{3,7}$]decan-4-yl)-5-chloro-3-ethyl-2,3-dihydro-2-oxo-1H-benzimidazole-1-carboxamide.

14. A compound according to claim 8 which is exo-N-(1-azatricyclo[3.3.1.1$^{3,7}$]decan-4-yl) -3-ethyl-2,3-dihydro-2-oxo-1H-benzisidazole-1-carboxamide.

15. A compound according to claim 8 which is exo-N-(1-azatricyclo[3.3.1.1$^{3,7}$]decan-4-yl)-6-chloro-3-ethyl-2,3-dihydro-2-oxo-1H-benzimidazole-1-carboxamide.

16. A compound according to claim 8 which is exo-N-(1-azatricyclo[3.3.1.1$^{3,7}$]decan-4-yl)-5-chloro-3-ethyl-2,3-dihydro-2-oxo-1H-benzimidazole-1-carboxamide.

17. A compound according to claim 8 which is endo-N-(1-azatricyclo[3.3.1.1$^{3,7}$]decan-4-yl)-2,3-dihydro-3-(1-methylethyl)-2-oxo-1H-benzimidazole-1-carboxamide.

18. A compound according to claim 8 which is exo-N-(1-azatricyclo[3.3.1.1$^{3,7}$]decan-4-yl)-2,3-dihydro-3-(1-methylethyl)-2-oxo-1H-benzimidazole-1-carboxamide.

19. A compound according to claim 8 which is exo-N-(1-azatricyclo[3.3.1.1$^{3,7}$]decan-4-yl)-6-chloro-2,3-dihydro-3-(1-methylethyl)-2-oxo-1H-benzimidazole-1-carboxamide.

20. A pharmaceutically composition comprising a therapeutically effective amount of a compound of the formula

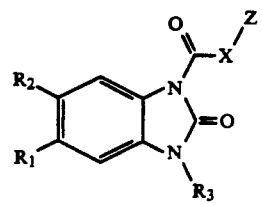

or a pharmaceutically acceptable salt thereof
wherein R$_1$ and R$_2$ are independently selected from the group consisting of hydrogen, alkoxy, halogen, amino, monoalkylamino, dialkylamino, acylamino and alkylsulfonylamino;
R$_3$ is selected from the group consisting of H, alkyl and cycloalkyl;
X is NH or O;
Z is selected from the group consisting of

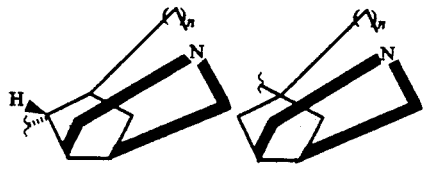

n and r are independently 1 or 2;
p is 0 or 1; and
a pharmaceutically acceptable carrier.

21. A pharmaceutical composition according to claim 20 wherein the compound is endo-N-(1-azatricyclo[3.3.1.1$^{3,7}$]decan-4-yl)-3-ethyl-2,3-dihydro-2-oxo-1H-benzimidazole-1-carboxamide.

22. A pharmaceutical composition according to claim 20 wherein the compound is endo-N-(1-azatricyclo[3.3.1.1$^{3,7}$]decan-4-yl)-6-chloro-2,3-dihydro-3-(1-methylethyl)-2-oxo-1H-benzimidazole-1-carboxamide.

23. A pharmaceutical composition according to claim 20 wherein the compound is endo-N-(1-azatricyclo[3.3.1.1$^{3,7}$]decan-4-yl)-5-chloro-2,3-dihydro-3-(1-methylethyl)-2-oxo-1H-benzimidazole-1-carboxamide.

24. A pharmaceutical composition according to claim 20 wherein the compound is endo-N-(1-azatricyclo[3.3.1.1$^{3,7}$]decan-4-yl)-6-chloro-3-ethyl-2,3-dihydro-2-oxo-1H-benzimidazole-1-carboxamide.

25. A pharmaceutical composition according to claim 20 wherein the compound is endo-N-(1-azatricyclo[3.3.1.1$^{3,7}$]decan-4-yl)-5-chloro-3-ethyl-2,3-dihydro-2-oxo-1H-benzimidazole-1-carboxamide.

26. A pharmaceutical composition according to claim 20 wherein the compound is exo-N-(1-azatricyclo[3.3.1.1^{3,7}]decan-4-yl) -3-ethyl-2,3-dihydro-2-oxo-1H-benzimidazole-1-carboxamide.

27. A pharmaceutical composition according to claim 20 wherein the compound is exo-N-(1-azatricyclo[3.3.1.1^{3,7}]decan-4-yl)-6-chloro-3-ethyl-2,3-dihydro-2-oxo-1H-benzimidazole-1-carboxamide.

28. A pharmaceutical composition according to claim 20 wherein the compound is exo-N-(1-azatricyclo[3.3.1.1^{3,7}]decan-4-yl)-5-chloro-3-ethyl-2,3-dihydro-2-oxo-1H-benzimidazole-1-carboxamide.

29. A pharmaceutical composition according to claim 20 wherein the compound is endo-N-(1-azatricyclo[3.3.1.1^{3,7}]decan-4-yl)-2,3-dihydro-3-(1-methylethyl)-2-oxo-1H-benzimidazole-1-carboxamide.

30. A pharmaceutical composition according to claim 20 wherein the compound is exo-N-(1-azatricyclo[3.3.1.1^{3,7}]decan-4-yl) -2,3-dihydro-3-(1-methylethyl)-2-oxo-1H-benzimidazole-1-carboxamide.

31. A pharmaceutical composition according to claim 20 wherein the compound is exo-N-(1-azatricyclo[3.3.1.1^{3,7}]decan-4-yl)-6-chloro-2,3-dihydro-3-(1-methylethyl)-2-oxo-1H-benzimidazole-1-carboxamide.

32. A method of treating conditions responsive to treatment with 5-HT$_4$ and 5-HT$_3$ agents comprising administering to a subject in need of such treatment a therapeutically effective amount of a compound of the formula

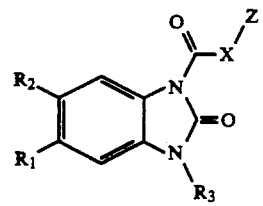

or a pharmaceutically acceptable salt thereof
wherein R$_1$ and R$_2$ are independently selected from the group consisting of hydrogen, alkoxy, halogen, amino, monoalkylamino, dialkylamino, acylamino and alkylsulfonylamino;
R$_3$ is selected from the group consisting of H, alkyl and cycloalkyl;
X is NH or O;
Z is selected from the group consisting of

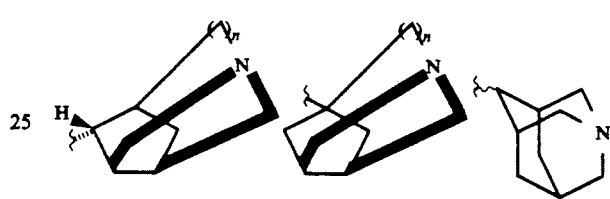

33. A method according to claim 32 wherein the condition is treatable with a serotonin 5-HT$_4$ agonist.

34. A method according to claim 33 wherein the condition is selected from the group consisting of esophagitis, non-ulcer dyspepsia, gastroparesis, ileus, constipation predominant irritable bowel syndrome, constipation and cognitive dysfunction.

35. A method according to claim 32 wherein the condition is treatable with a serotonin 5-HT$_4$ antagonist.

36. A method according to claim 35 wherein the condition is selected from the group consisting of diarrhea or diarrhea predominant irritable bowel syndrome.

37. A method according to claim 32 wherein the condition is treatable with a serotonin 5-HT$_3$ antagonist.

38. A method according to claim 37 wherein the condition is selected from the group consisting of emesis, anxiety, cognitive disorders, drug abuse and diarrhea predominant irritable bowel syndrome.

* * * * *

UNITED STATES PATENT AND TRADEMARK OFFICE
CERTIFICATE OF CORRECTION

PATENT NO. : 5,280,028
DATED : January 18, 1994
INVENTOR(S) : Flynn, et al.

It is certified that error appears in the above-indentified patent and that said Letters Patent is hereby corrected as shown below:

Column 1, line 23, reading "hydroxytryptanine;" should read -- hydroxytryptamine; --.

Column 1, line 45, reading "serotonings" should read -- serotonin's --.

Column 4, line 46, reading "(1977))." should read -- (1977)]. --.

Column 4, line 53, reading "exciplent," should read -- excipient, --.

Column 5, line 10, reading ""monoalkylazino"" should read -- "monoalkylamino" --.

Column 5, line 13, reading ""dialkylazino"" should read -- "dialkylamino" --.

Column 5, line 23, reading ""alkylsulfonylanino"" should read -- "alkylsulfonylamino" --.

Column 5, line 26, reading ""cycloaky"" should read -- "cycloalkyl" --.

Column 5, line 38, reading "mucosas" should read -- mucosae --.

Column 13, line 27, reading "(1987))" should read -- (1987)] --.

Column 14, line 20, reading "HCl" should read -- HCl* --.

Column 15, line 59, reading "HCl" should read -- *HCl --.

UNITED STATES PATENT AND TRADEMARK OFFICE
CERTIFICATE OF CORRECTION

PATENT NO. : 5,280,028
DATED : January 18, 1994
INVENTOR(S) : Flynn, et al.

It is certified that error appears in the above-indentified patent and that said Letters Patent is hereby corrected as shown below:

Column 16, line 20, reading "204" should read -- 20% --.

Column 16, line 23, reading "aninoethyl" should read -- aminoethyl --.

Column 16, line 25, reading "0.5 $\mu$l" should read -- 0.5 ml --.

Column 16, line 37, reading "*1.25" should read -- *1 HCl* 1.25 --.

Column 17, line 17, reading "HCl" should read -- HCl* --.

Column 18, line 45, reading "HCl" should read -- HCl* --.

Column 19, line 25, reading "HCl" should read -- HCl* --.

Column 20, line 4, reading "0.75" should read -- 0.75 H$_2$O --.

Column 22, line 6, reading "1 hr." should read -- 1 hr., --.

Column 22, line 67, reading "H$_2$O 0.75" should read --*H$_2$O*0.75 --.

Column 26, line 10, the part of formula reading

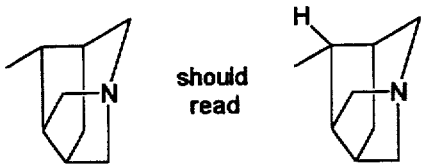

UNITED STATES PATENT AND TRADEMARK OFFICE
CERTIFICATE OF CORRECTION

PATENT NO. : 5,280,028
DATED : January 18, 1994
INVENTOR(S) : Flynn, et al.

It is certified that error appears in the above-indentified patent and that said Letters Patent is hereby corrected as shown below:

Column 26, line 37, reading "EP 454,121)" should read -- EP 454,121] --.

Column 29, line 67, reading "mucosas." should read -- mucosae. --.

Column 30, line 4, reading "Tyrodets" should read -- Tyrode's --.

Column 31, line 60, reading "benzisidazole" should read -- benzimidazole --.

Column 32, line 13, reading "pharmaceutically" should read -- pharmaceutical --.

Column 32, line 46, reading "n and r are independently 1 or 2; p is 0 or 1; and a pharmaceutically acceptable carrier" should read -- n is 1 or 2. --

Column 34, line 28, after the structure should read -- n is 1 or 2. --.

Signed and Sealed this

Twenty-eight Day of February, 1995

*Attest:*

BRUCE LEHMAN

*Attesting Officer*    *Commissioner of Patents and Trademarks*